US008278041B2

(12) United States Patent
Levin (10) Patent No.: US 8,278,041 B2
(45) Date of Patent: Oct. 2, 2012

(54) COMPOSITIONS AND METHODS FOR DETECTING FOOD-BORNE PATHOGENS (75) Inventor: Robert E. Levin, Amherst, MA (US)

(73) Assignee: InfrAegis, Inc., Elk Grove Village, IL (US)

( * ) Notice: Subject to any disclaimer, the term of this patent is extended or adjusted under 35 U.S.C. 154(b) by 313 days.

(21) Appl. No.: 12/589,463

(22) Filed: Oct. 23, 2009

(65) Prior Publication Data

US 2010/0129813 A1 May 27, 2010

Related U.S. Application Data (60) Provisional application No. 61/108,740, filed on Oct. 27, 2008.

(51) Int. Cl.
*C12Q 1/68* (2006.01)
(52) U.S. Cl. ......................................................... 435/6.1
(58) Field of Classification Search .................. None
See application file for complete search history.

(56) References Cited

U.S. PATENT DOCUMENTS

| | | | |
|---|---|---|---|
| 3,337,612 A | 8/1967 | Sharps | |
| 3,865,240 A | 2/1975 | Schick | |
| 5,210,015 A | 5/1993 | Gelfand et al. | |
| 5,320,773 A * | 6/1994 | Perman et al. | 252/191 |
| 5,487,972 A | 1/1996 | Gelfand et al. | |
| 5,488,021 A | 1/1996 | DeLiso et al. | |
| 5,591,118 A | 1/1997 | Bierck | |
| 6,300,069 B1 | 10/2001 | Missel et al. | |
| 6,740,406 B2 | 5/2004 | Hu et al. | |
| 2002/0110689 A1 * | 8/2002 | Hu et al. | 428/375 |

OTHER PUBLICATIONS

Fortin, N.Y. et al., "Use of Real-Time Polymerase Chain Reaction and Molecular Beacons for the Detection of *Escherichia coli* O 175:H7," *Analytical Biochemistry*, 289, 281-288 (2001).
Wang, Shishan et al., "Discrimination of viable *Vibrio vulnificus* cells from dead cells in real-time PCR," *Journal of Microbiological Methods*, 64 (2006) 1-8.
Luan, Chunguang et al., "Use of activated carbon coated with bentonite for increasing the sensitivity of per detection of *Escherichia coli* O157:H7 in Canadian oyster (*Crassostrea gigas*) tissue," *Journal of Microbiological Methods*, 72 (2008) of 67-72.
Abolmaaty, A. et al., "The use of activated charcoal for the removal of PCR inhibitors from oyster samples," *Journal of Microbiological Methods*, 68 (2007) 349-352.

* cited by examiner

*Primary Examiner* — Christopher M. Babic
(74) *Attorney, Agent, or Firm* — McDermott Will & Emery LLP (57) ABSTRACT

The present invention provides formulations and methods for isolating food-borne pathogens from a great variety of food matrices. Methods for isolating microorganisms from clinical and environmental specimens are also disclosed. The invention also concerns methods for rapid and efficient isolation of sufficiently pure DNA from small amounts of various pathogenic microorganisms, which then can be used, according to the methods of the instant invention, for selective identification of a live pathogenic microorganism present in a sample from which the microorganism was isolated. The methods of the instant invention are also useful for identification of new pathogenic microorganisms, diagnostics of food-borne illnesses, treatment of food-borne diseases and quality control of food items offered for sale to consumers.

18 Claims, 4 Drawing Sheets

COMPOSITIONS AND METHODS FOR DETECTING FOOD-BORNE PATHOGENS

CROSS-REFERENCE TO RELATED APPLICATIONS

This application claims priority to U.S. Provisional Patent Application Ser. No. 61/108,740, filed Oct. 27, 2008, which is expressly incorporated herein by reference.

FEDERALLY SPONSORED RESEARCH OR DEVELOPMENT

Not Applicable.

TECHNICAL FIELD

The present subject matter relates to compositions and methods for rapidly detecting food-borne pathogens from a variety of samples, including without the limitation, food samples, human tissues, human fluids, animal tissues, animal fluids, plant tissues, clinical specimens or environmental specimens.

BACKGROUND

More than 200 known diseases are transmitted through food. The causes of food-borne illness include viruses, bacteria, parasites, toxins, metals, and prions. See "Computerized Teaching Materials for the Infectious Diseases Course at KCOM" by Dr. Neal Chamberlain. The symptoms of food-borne illness range from mild gastroenteritis to life-threatening neurological (for example, botulism; *Clostridium botulinum*), hepatic (for example, Hepatitis A), and renal syndromes (for example, *E. coli* O157:H7). Food-borne diseases cause about 76 million illnesses, 325,000 hospitalizations, and 5,000 deaths in the United States each year. Known pathogens account for an estimated 14 million illnesses, 60,000 hospitalizations, and 1,800 deaths with *Salmonella*, *Listeria*, and *Toxoplasma*, being responsible for 1,500 deaths each year. Unknown agents account for the remaining 62 million illnesses, 265,000 hospitalizations, and 3,200 deaths.

According to data reported by Mead et al. 1999, the following are the most common microbial causes of food-borne illnesses.

TABLE 1

Most Common Microbial Causes of Food-borne Illness

| Disease or Agent | Estimated Total Cases | Percentage of Food-Borne Transmission |
| --- | --- | --- |
| Noroviruses (Norwalk-like viruses) | 23,000,000 | 40 |
| *Campylobacter* species | 2,500,000 | 80 |
| *Giardia lamblia* | 2,000,000 | 10 |
| *Salmonella* | 1,400,000 | 95 |
| *Shigella* | 450,000 | 20 |
| *Cryptosporidium parvum* | 300,000 | 10 |
| *Clostridium* species | 250,000 | 100 |
| *Toxoplasma gondii* | 225,000 | 50 |
| *Staphylococcus aureus* | 185,000 | 100 |
| Shiga toxin-producing *Escherichia coli* (STEC) | 110,000 | 85 |
| *Yersinia enterocolitica* | 100,000 | 90 |
| *Bacillus cereus* | 27,000 | 100 |
| *Cyclospora cayetanensis* | 16,000 | 90 |
| *Listeria monocytogenes* | 2,500 | 99 |

Surveillance of food-borne illnesses is complicated by the fact that a proportion of such diseases is caused by pathogens or agents that have not yet been identified and thus cannot be diagnosed. Further, many of the pathogens that are of greatest concern today (e.g., *Campylobacter jejuni*, *Escherichia coli* O157:H7, *Listeria monocytogenes*, *Cyclospora cayetanensis*) were not recognized as causes of food-borne illness just 20 years ago. Therefore, there remains the need for developing better methods for detecting microbial food-borne pathogens.

Due to interference of various inhibitors, tests for pathogens were limited to sample sizes of about 25 grams at their maximum. As a result, testing of large amounts of specimens, such as raw or uncooked foodstuffs, required numerous tests in order to verify the specimen did not contain pathogens. Such testing was tedious and expensive because a significant amount of tests were needed to verify that no pathogens existed in the specimen. Accordingly, a need also exists for testing sample sizes greater than what is conventionally available while obviating the problems associated with conventional methods.

The instant invention aims to address this need by providing methods and compositions for rapid and accurate detection of microbial and viral pathogens in food samples.

SUMMARY

In one embodiment, the instant invention concerns a composition for purification of a microorganism or parasite from a sample, which comprises activated charcoal coated with bentonite. The ratio of bentonite to activated charcoal in the composition may be in the range from 1:2 to 1:20. According to the embodiments of the instant invention, the composition may be used to purify microorganisms from food samples, human tissues, human fluids, animal tissues, animal fluids, plant tissues, clinical specimens or environmental specimens. In some embodiments, a composition of activated charcoal coated with bentonite may be pre-packed in a column. The embodiments of the instant invention include a method for preparing activated charcoal coated with bentonite, in which activated charcoal powder is washed with deionized water, and a suspension of bentonite in deionized water is then prepared; the washed activated charcoal powder is then mixed with the bentonite suspension, and the resulting activated charcoal coated with bentonite mixture is permitted to dry completely. In some embodiments, bentonite and activated charcoal can be mixed in the ratio of bentonite to activated charcoal in the range from 1:2 to 1:20. In other embodiments, bentonite and activated charcoal can be mixed in the ratio of bentonite to activated charcoal 1:6. In yet other embodiments, bentonite and activated charcoal are mixed in the ratio of bentonite to activated charcoal 1:16.

The embodiments of the instant invention also include a method for preparing activated charcoal coated with bentonite, in which activated charcoal powder is washed with deionized water, and a suspension of bentonite in deionized water is then prepared; the washed activated charcoal powder is then mixed with the bentonite suspension by shaking the mixture for 12 hours at 37° C., and the resulting activated charcoal coated with bentonite mixture is permitted to dry completely. The embodiments of the instant invention also include a method for preparing activated charcoal coated with bentonite, in which activated charcoal powder is washed with deionized water, and a suspension of bentonite in deionized water is then prepared; the washed activated charcoal powder is then mixed with the bentonite suspension, and the resulting activated charcoal coated with bentonite mixture is permitted to dry completely by letting the mixture stay for 3 to 4 hours at 55° C.

Other embodiments of the instant invention include a method for preparing activated charcoal coated with bentonite, in which 16.3 g of activated charcoal powder is washed with deionized water and 30 ml packed wet volume of the washed activated charcoal powder is obtained. Four grams of bentonite is then added to 200 ml of deionized water and blended at high speed for 1 minute in a blender jar, followed by centrifugation of the resulting bentonite/water suspension and obtaining 130 ml of the top bentonite suspension. 30 ml of packed wet volume of the washed activated charcoal powder is then mixed with the 130 ml of bentonite suspension by shaking the charcoal/bentonite mixture at 150 rpm during 12 hours at 37° C.; and the resulting activated charcoal coated with bentonite is then obtained by letting the mixture to dry completely by incubating the mixture for 12 to 48 hours at 55° C. It will be understood that drying time is related to and depends on the size of the batch being processed.

Yet in other embodiments, the instant invention concerns a method for removing polymerase chain reaction (PCR) inhibitors from a sample comprising a pathogenic microorganism or parasite, in which the sample is incubated with activated charcoal coated with bentonite prior to DNA extraction from the microorganism and performance of DNA analysis. The method may be used for removing PCR inhibitors from samples such as food samples, human tissues, human fluids, animal tissues, animal fluids, plant tissues, clinical specimens or environmental specimens. In some embodiments, the weight ratio of bentonite to activated charcoal in the method for removing PCR inhibitors is in the range from 1:2 to 1:20. DNA analysis procedures for which the above-described method is useful include DNA cloning, Southern blot analysis, slot-blot analysis, in situ hybridization, DNA sequencing, hybridization with a probe, incubation with a fluorescent dye, PCR, real-time PCR, DNA chromatography, flow-cytometry, in vitro transcription, in vitro translation, binding reactions with antibodies or binding reactions with proteins. In the disclosed methods for removing PCR inhibitors, the activated charcoal coated with bentonite can be prepared as follows: activated charcoal is washed with deionized water and a suspension of bentonite in deionized water is also prepared; the washed activated charcoal powder is then mixed with the bentonite suspension, and the resulting activated charcoal coated with bentonite mixture is permitted to dry completely. In some embodiments of the disclosed methods, a sample can be incubated with activated charcoal coated with bentonite at a pH in the range from 5 to 8. In other embodiments of the disclosed methods, a sample can be incubated with activated charcoal coated with bentonite at a pH in the range from 4.5 to 5.5. Yet in other embodiments of the disclosed methods, a sample can be incubated with activated charcoal coated with bentonite at pH equal five. At least in some embodiments of the methods, a sample can be incubated with activated charcoal coated with bentonite by passing the sample at least once through a column packed with activated charcoal coated with bentonite.

According to some embodiments of the disclosed methods, the weight ratio of the sample to the charcoal may be in the range from 1:1 to 20:1. In at least some embodiments of the instant invention, the sample can be incubated with β-cyclodextrin prior to its incubation with activated charcoal coated with bentonite. β-cyclodextrin may be used as a 10% solution. The incubation of a sample with β-cyclodextrin can be performed by completing the following steps: homogenizing a sample with β-cyclodextrin during 1 to 10 minutes at room temperature; centrifuging the resulting homogenate of step 1 at 1,000 rpm to 3,000 rpm during 1 to 5 minutes; and collecting a supernatant comprising the pathogenic microorganism. According to the disclosed methods, the following cyclodextrins can be used: α-cyclodextrin, β-cyclodextrin and γ-cyclodextrin.

In at least some of its embodiments, the instant invention concerns a method for isolating a microorganism or parasite from food samples, animal tissues, human tissues, human fluids, plant tissues, environmental or clinical specimens. The following steps are performed in the method: 1) one weight part of sample, tissue, fluids or specimen is homogenized in 2 to 10 parts of saline comprising from 0.2% to 1.0% of sodium chloride; 2) a β-cyclodextrin solution is added to the homogenized sample of step 1; 3) the mixture of step 2 is blended to homogeneity; 4) the homogenized mixture of step 3 is centrifuged at 1,000 rpm to 3,000 rpm for 1 to 5 minutes; 5) a supernatant fraction is collected after centrifugation of step 4; 6) the supernatant fraction of step 5 is further centrifuged at 8,000 rpm to 15,000 rpm for 5 to 10 minutes at 4° C. to obtain a liquid fraction and a pellet; 7) the liquid is discarded and the pellet of step 6 is resuspended in sterile saline to obtain a suspension; 8) the pH of the resulting suspension is adjusted to a pH in the range from 4.5 to 6; 9) the suspension of step 8 is incubated with activated charcoal coated with bentonite; 10) the suspension is centrifuged after the treatment of step 9 at 8,000 rpm to 15,000 rpm for 5 to 20 minutes and obtaining the pellet; and 11) the pellet of step 10 is resuspended in a sterile saline.

The instant invention also concerns a method for extracting DNA from a microorganism or parasite or parasite's eggs, comprising the following steps: 1) isolating the microorganism by performing the method as described above; 2) releasing DNA from the microorganism by boiling the isolated microorganism in a solution comprising 2% Triton X-100, 2.5 mg/ml sodium azide, 0.1M Tris-HCl, pH 8.0; and 3) precipitating the resulting DNA with chilled ethanol.

The instant invention also concerns a method for extracting DNA from a microorganism, comprising the following steps: 1) isolating the microorganism by performing the method as described above; 2) releasing DNA from the microorganism by boiling the isolated microorganism in a solution comprising DNA carrier, 2% Triton X-100, 2.5 mg/ml sodium azide, 0.1M Tris-HCl, pH 8.0; and 3) precipitating the resulting DNA with chilled ethanol. At least in some of the embodiments, the DNA carrier may be selected from BSA, high molecular weight DNA, yeast genomic DNA, salmon sperm DNA or a combination of any of these carriers.

The instant invention also concerns a method for identification of a live microorganism or parasite in a food sample, tissue, environmental or clinical specimen, in which the following steps are performed: 1) homogenizing a food sample, tissue, environmental or clinical specimen comprising a pathogenic microorganism with saline; 2) incubating the resulting homogenate of step 2 with β-cyclodextrin; 3) centrifuging the mixture of step 2 at 1,000 to 3,000 rpm for 3 to 15 minutes and obtaining a supernatant and a pellet; 4) collecting the supernatant from step 3; 5) centrifuging the supernatant of step 4 at 8,000 to 15,000 rpm for 5 to 20 minutes; 6) resuspending the pellet obtained from centrifugation of step 5 in sterile saline thereby obtaining a suspension; 7) incubating the suspension of step 6 with activated charcoal coated with bentonite and collecting the resulting supernatant; 8) centrifuging the resulting supernatant of step 7 at 8,000 to 15,000 rpm for 5 to 20 minutes, thereby obtaining a pellet; 9) washing the resulting pellet of step 8 and resuspending the pellet in a lysing solution comprising 2% Triton X-100, 2.5 mg/ml sodium azide, 0.1M Tris-HCl, pH 8.0; 10) boiling the mixture of step 9; 11) centrifuging the mixture of step 10, thereby obtaining a supernatant and a pellet; 12) precipitating DNA of the pathogenic microorganism from the supernatant of step 11 with chilled ethanol; 13) washing the precipitate of step 12; 14) resuspending the precipitate of step 13 in water, wherein the precipitate comprises DNA of the pathogenic microorganism; and 15) performing real-time PCR on the DNA obtained in step 14; wherein the intensity of real-time PCR in step 15 correlates with the presence of a live microorganism in the sample, tissue or specimen. Various microorganisms, including pathogenic microorganisms, can be identified by the above-described method.

In other embodiments, the instant invention concerns a method for identification of an optimal dosage of an antibiotic or other agent required to destroy or inhibit the growth of a live microorganism, in which samples infected with the same amount of a live microorganism or parasite are treated with various dosages of an antibiotic or other agent, the samples are then analyzed for the presence of live microorganisms, as described above. In another example, the optimal dosage of a food preservative or preservatives for addition to foodstuffs required for destroying or inhibiting the growth of a live microorganism may be identified. In one example, the method for identification of an optical dosage includes the steps of: obtaining a set of food samples, tissues, environmental or clinical specimens, said set comprising food samples, environmental or clinical specimens which were collected after treatment with various dosages of the antibiotic or other agent; identifying a live organism in the each of the samples or specimens in the sets described herein, thereby obtaining information about presence of a live microorganism and its quantity in each sample or specimen of the set; interpreting the information obtained, thereby identifying a sample or specimen in the set in which no live microorganisms were present or only a minimal number of live microorganisms was present in comparison to other samples or specimens in the set; and identifying the dosage of the antibiotic or other agent recorded which corresponds to the sample or specimen identified, wherein the dosage identified is the optimal dosage required to eliminate the live microorganism.

The instant invention also concerns a method for identification of an antibiotic or other agent suitable to destroy or inhibit growth of a live microorganism or parasite. In this method, samples infected with a microorganism or parasite are treated with various antibiotics or other agents, the samples are then analyzed for the presence of a live microorganism, according to a method described above. In one example, the method of identification of an antibiotic or other agent comprises the following steps: performing treatments with various antibiotics or other agents and recording an antibiotic or other agent used in each treatment; obtaining a set of food samples, environmental or clinical specimens, said set comprising food samples, environmental or clinical specimens which were collected after treatment with various antibiotics or other agents; identifying a live organism in each of the samples or specimens in the set obtained as described herein, thereby obtaining information about presence of a live microorganism and its quantity in each sample or specimen of the set; interpreting the information obtained, thereby identifying a sample or specimen in the set in which no live microorganisms were present or only a minimal number of live microorganisms was present in comparison to other samples or specimens in the set; and identifying the antibiotic or other agent recorded which corresponds to the sample or specimen identified, wherein the antibiotic or other agent identified is suitable to eliminate the live microorganism.

Methods of the instant invention also include those which can be used to identify a pathogenic microorganism or parasite in a sample. In these methods, a sample suspected to comprise a microorganism or parasite is treated with activated charcoal coated with bentonite, microbial DNA is then extracted from the sample, and sample is then subjected to DNA analysis. Various samples can be analyzed according to the above-described method, including food samples, human tissues, human fluids, animal tissues, animal fluids, plant tissues, clinical specimens or environmental specimens. In these methods, the weight ratio of bentonite to activated charcoal is in the range from 1:2 to 1:20. In these methods. DNA analysis may include at least on of the following: DNA cloning, Southern blot analysis, slot-blot analysis, in situ hybridization, DNA sequencing, hybridization with a probe, incubation with a fluorescent dye, PCR, real-time PCR, DNA chromatography, flow-cytometry, in vitro transcription, in vitro translation, binding reactions with antibodies or binding reactions with proteins.

Methods of the instant invention also include those that can be used for diagnosing a food-borne illness in a patient. In these methods, a food sample or specimen is obtained from the patient; and the microorganism or parasite present in the sample or specimen is identified as described above. Methods of the instant invention also include methods of treatment of a food-borne illness in a patient. According to those methods, a microorganism or parasite that causes the food-borne illness in the patient is identified as described above, and the patient is then treated with an antibiotic known to be efficient against the identified microorganism.

The instant invention also concerns a kit for isolating a food-borne pathogen, which includes a column filled with activated charcoal coated with bentonite. Such kits can be used for isolating a pathogen from food samples, human tissues, human fluids, animal tissues, animal fluids, plant tissues, clinical specimens and environmental specimens.

The instant methods and compositions surprisingly allow for use of sample sizes much larger than conventional sample sizes. For example, sample sizes up to and including about 500 grams may be used in the present disclosure without interference from inhibitors. In one example, samples of a foodstuff are obtained from, for example, various portions of a field, food processing and/or distribution facility, or other location having foodstuffs. The samples are obtained in an amount, for example, of about 25 grams. The samples are then combined to yield a sample size of about 250 grams to about 500 grams. The resultant combined sample is then processed and analyzed according to the methods of the present invention.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the compositions, methodologies, instrumentalities and combinations set forth in the detailed examples and embodiments discussed below.

Figure 1:
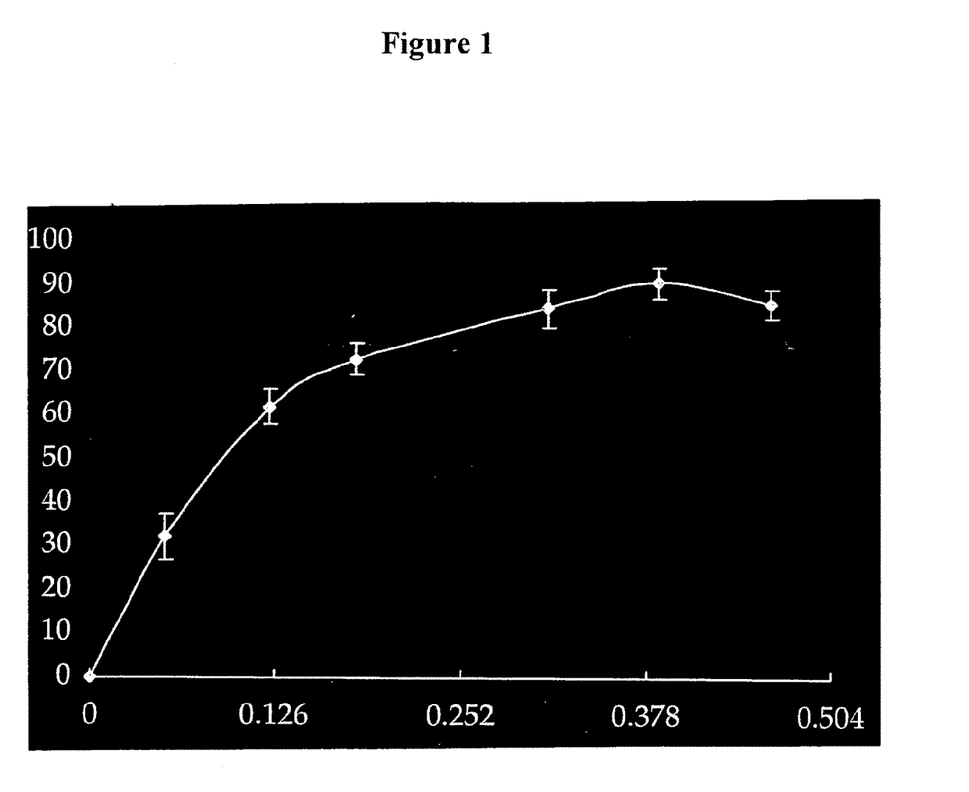
FIG. 1 is an example showing that recovery of *E. Coli* O157:H7 from activated charcoal coated with bentonite depends on the weight ratio of bentonite to activated charcoal.

The percentage of *E. Coli* O157:H7 cells (axis Y) depends on the amount of bentonite (axis X) used to coat 4.2 g of activated carbon.

FIG. 2 is an example showing selective detection and quantification of live bacterial cells from mixtures of live and heat-inactivated cells by real-time PCR. Part (A) is an example showing a typical agarose gel image of PCR amplified products. The total number of genomic DNA per PCR reaction was kept constant at $1.0\times10^5$/PCR, while the number of live cells (in CFU/PCR) was varied in lines 1-7 as follows: $1\times10^2$; $3.2\times10^2$; $1\times10^3$; $1\times10^4$; $3.2\times10^4$ and $1\times10^5$. Part (B) is an example showing that the relative fluorescent intensity of amplified DNA (axis Y) is directly dependent on the logarithmic number of genomic targets from life cells in the mixtures of life and heat-inactivated cells (axis X).

FIG. 3 is an example showing the effect of γ-irradiation on amplification efficiency of real-time PCR assays. DNA templates derived from $1.0\times10^3$ CFU were prepared from irradiated *V. vulnificus* and incorporated into real-time PCR assays with four different primer pairs. (A) VV1000F/VV1000R, (B) VV700F/VV700R, (C) VV300F/VV300R and (D) VV70F/VV70R respectively. The inset shown in (C) is an example of an image of real-time PCR amplified products of irradiated *V. vulnificus* (C: control, and lines 1-3: 0, 1.08, 3.0, and 5.0 KGy respectively).

FIG. 4 is an example showing that purification of bacterial DNA in the presence of DNA carriers decreases the threshold value (Ct) in real-time PCR reactions with DNA specific primers.

♦ Broth+BSA+DNA; ■ Tissue Concentrate; ▲ Tissue+BSA+DNA.

DETAILED DESCRIPTION

In the following detailed description, numerous specific details are set forth by way of examples in order to provide a thorough understanding of the relevant teachings. While the invention is susceptible of embodiments in many different forms, preferred embodiments will be described herein in detail with the understanding that the present disclosure is to be considered an exemplification of the principles of the invention and is not intended to limit the broad scope of the invention. However, it should be apparent to those skilled in the art that the present teachings may be practiced without such details. In other instances, well known methods, procedures, compositions and/or components have been described at a relatively high-level, without detail, in order to avoid unnecessarily obscuring aspects of the present teachings.

In one embodiment, the invention concerns rapid and accurate methods for detecting food-borne pathogens, including without limitation, parasites and their eggs, Noroviruses (Norwalk-like viruses), *Campylobacter* species, *Giardia lamblia, Salmonella, Shigella, Cryptosporidium parvum, Clostridium species, Toxoplasma gondii, Staphylococcus aureus*, Shiga toxin-producing *Escherichia coli* (STEC), *Yersinia enterocolitica, Bacillus cereus, Bacillus anthracis, Cyclospora cayetanensis, Listeria monocytogenes, Listeria monocytogenes, Vibrio parahemolyticus* and *V. vulnificus*. The term "microorganism" as used in this disclosure includes a virus, bacterium, parasite or parasite's egg.

In another embodiment, the invention concerns rapid and efficient methods for detecting pathogenic microorganisms from a variety of samples, including without the limitation, food samples, environmental and clinical specimens.

In a further embodiment, the invention concerns methods that permit efficient extraction of bacteria, viruses and parasites from a wide variety of complex food matrices, including without the limitation, raw seafood, raw eggs, undercooked meat or poultry, unpasteurized milk or juice, unpasteurized soft cheeses, home-made canned goods, raw hot dogs, deli meats, ground beef, poultry, meat, rice, shellfish, prepared food, salads, sandwiches, fruit, gravy and fresh produce. Therefore, the disclosed methods are useful for diagnosing and treating food-borne illnesses as well for performing quality-control tests of consumer food products.

In one embodiment, the invention concerns methods which utilize activated charcoal coated with bentonite for collecting food-borne pathogens from various food samples. In another embodiment, the invention concerns formulations of activated charcoal coated with bentonite and methods for preparing the same. The formulations include those in which the ratio of bentonite to activated charcoal is from 1:2 to 1:20. The ratio between bentonite and activated charcoal can be 1:4, 1:5, 1:6, 1:7 or 1:8. In one embodiment, the ratio between bentonite and activated charcoal is 1:6. In another embodiment, the ratio between bentonite and activated charcoal is 1:16.

The present invention also concerns methods for preparing formulations of activated charcoal coated with bentonite. In one embodiment, activated charcoal powder which consists of 1 to 2 mm particles can be used. The activated charcoal powder is washed several times with water and then mixed with bentonite homogenized into a suspension, preferably in deionized water. Bentonite and washed activated charcoal powder can be mixed at any of the following ratios: 1:2; 1:3; 1:4; 1:5; 1:6; 1:7; 1:8; 1:9; 1:10; 1:11; 1:12; 1:13; 1:14; 1:15; 1:16; 1:17; 1:18; 1:19; or 1:20. In one embodiment, bentonite and washed activated charcoal are mixed in the ratio 1:6. In another embodiment, bentonite and washed activated charcoal are mixed in the ratio 1:16.

In one embodiment, the mixing of the charcoal powder with the bentonite suspension is carried out at room temperature. In another embodiment, the mixing is carried out at 37° C. In yet further embodiments, the mixing can be carried out at any temperature in the range from 18° C. to about 45° C. The mixing can be carried out at any of the above temperatures from 1 hour to 24 hours. In one embodiment, the mixing is carried out for 10 hours with shaking at 37° C. In another embodiment, the mixing is carried out for 12 hours with shaking at 37° C. In yet further embodiment, the mixing is carried out for 14 hours with shaking at 37° C.

After the mixing is completed, activated charcoal coated with bentonite is allowed to dry. In one embodiment, activated charcoal coated with bentonite is dried at 55° C. from 2 hours to 8 hours. In another embodiment, activated charcoal coated with bentonite is dried at 55° C. from 3 to 4 hours. In yet further embodiment, activated charcoal coated with bentonite is dried at any temperature in the range from about 50° C. to about 100° C. for a period of time from about 30 minutes to about 48 hours. Activated charcoal coated with bentonite prepared according to the disclosed methods can be stored at room temperature.

The above-formulations of activated charcoal coated with bentonite can be used for purifying food-borne pathogens from different food samples. In one embodiment, the invention provides methods for obtaining food-borne pathogens from various food matrices. These methods utilize activated charcoal coated with bentonite and permit recovery of DNA samples that are free of polymerase chain reaction (PCR) inhibitors. In these methods, a food sample is homogenized and a fraction comprising food-borne pathogen is obtained by centrifugation. The fraction is then incubated with activated charcoal coated with bentonite preferably prepared as disclosed above. In one embodiment from 0.2 to 20 grams of activated charcoal coated with bentonite can be used for each 5 grams of the initial food sample. In another embodiment, 10 grams of activated charcoal coated with bentonite can be used for each 5 grams of the food sample. In yet further embodiment, 1 gram of activated charcoal coated with bentonite can be used for each 5 grams of the initial food sample. In yet another embodiment, 1 gram of activated charcoal coated with bentonite can be used for each 20 grams of the initial food sample.

The incubation of a food sample with activated charcoal coated with bentonite can be carried out at any temperature in the range from 4° C. to 37° C. In one embodiment, the incubation is carried out at room temperature, in another embodiment the incubation is carried out at 4° C. The incubation can be carried out with shaking for a period of time from 10 minutes to 2 hours. In one embodiment, activated charcoal coved with bentonite is packed into a column and a sample suspected of containing food-borne microorganisms is then passed through the column. The sample can be passed through the column several times. In yet another embodiment, activated charcoal coated with bentonite can be prepacked into a column and such columns can be stored at room temperature for a period of time from 1 week to 1 year or more prior to use. In yet another embodiment, columns with activated charcoal coated with bentonite can be included in a kit along with other components such as reagents for subsequent DNA purification and identification including reagents for control reactions.

In another embodiment, the invention concerns rapid and reliable methods for isolating a pathogen from a variety of samples, including without the limitation, environmental specimens, clinical specimens, animal tissues, human tissues, human fluids or plant tissues. In these methods, the sample is homogenized and a fraction suspected of comprising pathogenic microorganisms is obtained by centrifugation. The fraction is then incubated with activated charcoal coated with bentonite prepared as disclosed above. In one embodiment from 0.2 to 20 grams of activated charcoal coated with bentonite can be used for each 5 grams of the initial sample. In another embodiment, 10 grams of activated charcoal coated with bentonite can be used for each 5 grams of the initial sample. In yet further embodiment, 1 gram of activated charcoal coated with bentonite can be used for each 5 grams of the initial sample. In yet another embodiment, 1 gram of activated charcoal coated with bentonite can be used for each 20 grams of the initial sample.

The incubation of a sample with activated charcoal coated with bentonite can be carried out at any temperature in the range from 4° C. to 37° C. In one embodiment, the incubation can be carried out at room temperature, in another embodiment the incubation can be carried out at 4° C. The incubation can be carried out with shaking for a period of time from 10 minutes to 2 hours. In one embodiment, activated charcoal coated with bentonite is packed into a column and a sample suspected of containing food-borne microorganisms is then passed through the column. The sample can be passed through the column several times. In yet another embodiment, activated charcoal coated with bentonite can be prepacked into a column and such columns can be stored at room temperature for a period of time from 1 week to 1 year prior to use. In yet another embodiment, columns with activated charcoal coated with bentonite can be included in a kit along with other reagents for subsequent DNA purification.

The incubation of a sample with activated charcoal coated with bentonite can be performed at a pH in the range from 5 to 8. In one embodiment, the incubation is performed at pH 5. In another embodiment, the incubation is performed at pH 6.

Table 2 further explains that the efficiency of recovery of food-borne pathogens from activated charcoal coated with bentonite is dependent on a pH during the incubation, with the optimal pH being at about 5.0.

TABLE 2

The Percent Recovery of *E. coli* O157:H7 at different pH values after 4.2 g of activated charcoal was coated with 0.4 g of bentonite.

| | pH | | | | |
|---|---|---|---|---|---|
| | 4.0 | 5.0 | 6.0 | 7.0 | 8.0 |
| % of recovery | 0 | 91.6 ± 4.6 | 83.6 ± 3.2 | 75.2 ± 5.5 | 50.3 ± 4.2 |

In some other embodiments, a food sample can be incubated with β-cyclodextrin prior to incubation with activated charcoal coated with bentonite. This incubation with β-cyclodextrin is particularly useful when the need arises to separate a fraction comprising food-borne pathogens from fat comprising a food sample.

In these methods, a sample comprising food-borne microorganisms or other pathogenic microorganisms may be incubated with β-cyclodextrin prior to incubation with activated charcoal coated with bentonite. In these methods, a sample comprising food-borne microorganisms or other pathogenic microorganisms may also be incubated with β-cyclodextrin concurrently or subsequently to incubation with activated charcoal coated with bentonite.

In other embodiments, other cyclodextrins, such as, for example, α-cyclodextrin and γ-cyclodextrin can be used either instead of β-cyclodextrin or in a combination with it. In the above-methods, β-cyclodextrin or any other cyclodextrin can be used as a 5% solution. In other embodiments, β-cyclodextrin or any other cyclodextrin can be used as a 10% solution. Yet in further embodiments, β-cyclodextrin or any other cyclodextrin can be used as a 15% solution.

The optimal weight ratio between β-cyclodextrin or any other dextrin and a food sample or any other sample such as, for example, human tissue, animal tissue, clinical specimen or environmental specimen, depends at least in part on the amount of fat to be removed from the sample. The more fat the initial sample comprises, the more β-cyclodextrin or any other dextrin is required to efficiently remove the fat from the sample. In one embodiment, four weight parts of a 10% β-cyclodextrin solution can be used for one part of a sample. In another embodiment, from 1 to 10 weight parts of a 10% β-cyclodextrin solution can be used for one part of a sample. In a further embodiment, from 1 to 10 weight parts of a cyclodextrin solution can be used for one part of a sample. The incubation with β-cyclodextrin or any other cyclodextrin solution can be carried out at room temperature by mixing a homogenized sample, such as for example, food sample, with β-cyclodextrin or any other cyclodextrin, and subsequently centrifuging the mixture to separate a fraction comprising food-borne microorganisms from the remaining sample.

In yet another embodiment, the present invention concerns methods for DNA extraction from a microorganism, such as, for example, a virus, parasite, pathogenic microorganism or food-borne microorganism, which then can be analyzed by different methods, including, but not limited to, polymerase chain reaction (PCR), real time PCR, Southern blot analysis and in situ hybridization.

In one embodiment, prior to DNA extraction, a food sample is incubated with activated charcoal coated with bentonite prepared according to the above-disclosed methods. The incubation can be performed at room temperature from 10 minutes to one hour. Alternatively, the incubation can be performed at any temperature in the range from 37° C. to 4° C. In these methods, activated charcoal coated with bentonite can be packed into a column and a food sample can then be passed through the column at least once.

In yet another embodiment, a food sample can be incubated with a β-cyclodextrin solution prior to incubation with activated charcoal coated with bentonite. In one embodiment, a food sample is homogenized with a 10% β-cyclodextrin solution in the ratio 1 to 4 for 1 to 10 minutes, then centrifuged from 1,000 rpm to 3,000 rpm and food-borne microorganisms are collected as a liquid fraction which subsequently is incubated with activated charcoal coated with bentonite as described above.

After incubation with P-cyclodextrin and activated charcoal coated with bentonite, a sample comprising food-borne microorganisms can be subjected to incubation with a lysing solution formulated to disrupt bacterial cells and release DNA which can be then precipitated with ethanol. Any of lysing solutions suitable for disruption of bacterial cells can be used. In one embodiment, a TZ lysing solution comprising 2% Triton X-100, 2.5 mg/ml sodium azide and 0.1 M Tris-HCl, pH 8.0 can be used.

In at least some of the embodiments, DNA extracted from food-borne microorganisms can be further purified by using purification kits that are commercially available. Such kits, for example, include the Wizard® Clean-up system (Promega, Cat. No. A7170) and the QIamp® DNA Mini Kit (Qiagen, Cat. No. 51304).

The above-disclosed methods of the instant invention can be used for isolating DNA from a variety of food-borne microorganisms, including, without the limitation, parasites and their eggs, Noroviruses (Norwalk-like viruses), *Campylobacter* species, *Giardia lamblia, Salmonella, Shigella, Cryptosporidium parvum, Clostridium* species, *Toxoplasma gondii, Staphylococcus aureus,* Shiga toxin-producing *Escherichia coli* (STEC), *Yersinia enterocolitica, Bacillus cereus, Bacillus anthracis, Cyclospora cayetanensis, Listeria monocytogenes, Listeria monocytogenes, Vibrio parahemolyticus* and *V. vulnificus.*

The above-disclosed methods for DNA isolation can be used with a great variety of food matrices, including without the limitation, raw seafood, raw eggs, meat and poultry, unpasteurized milk or juice, unpasteurized soft cheeses, home-made canned goods, raw hot dogs, deli meats, ground beef, rice, shellfish, prepared foods, salads, sandwiches, fruit, gravy and fresh produce.

In yet another embodiment, the methods of the instant invention can be used for extracting DNA from a pathogenic microorganism isolated from an environmental specimen, clinical specimen and any of the human, plant or animal tissues or fluids.

In these embodiments, prior to DNA extraction, a sample is incubated with activated charcoal coated with bentonite prepared according to the above-disclosed methods. The incubation can be performed at room temperature from 10 minutes to one hour. Alternatively, the incubation can be performed at any temperature in the range from 37° C. to 4° C. In these methods, activated charcoal coated with bentonite can be packed into a column and a sample comprising pathogenic microorganism can then be passed through the column at least once.

In yet another embodiment, a food sample or any of the above tissue samples can be incubated with a β-cyclodextrin solution prior to incubation with activated charcoal coated with bentonite. In one embodiment, a food sample or a tissue sample is homogenized with a 10% β-cyclodextrin solution in the ratio 1 to 4 for 1 to 10 minutes, then centrifuged from 1,000 rpm to 3,000 rpm and food-borne microorganisms or other pathogenic microorganisms are collected as a liquid fraction which subsequently is incubated with activated charcoal coated with bentonite as described above.

After incubation with β-cyclodextrin and activated charcoal coated with bentonite, a sample comprising pathogenic microorganisms, including food-borne microorganisms, can be subjected to incubation with a lysing solution formulated to disrupt bacterial cells and release DNA which can be then precipitated with ethanol. Any of lysing solutions suitable for disruption of bacterial cells can be used. In one embodiment, a TZ lysing solution comprising 2% Triton X-100, 2.5 mg/ml sodium azide and 0.1 M Tris-HCl, pH 8.0 can be used.

In at least some of the embodiments, DNA extracted from pathogenic microorganisms can be further purified by using purification kits that are commercially available. Such kits, for example, include the Wizard® Clean-up system (Promega, Cat. No. A7170) and the QIamp® DNA Mini Kit (Qiagen, Cat. No. 51304).

In some of its embodiments, the present invention concerns different methods for analyzing DNA isolated from a food-borne pathogen. Such DNA analysis may include a test to determine which of the known food-borne pathogens and in what concentration are present in a particular food sample. In other embodiments, such analysis may be used to isolate and clone new food-borne pathogens. The results of the analysis may be used to determine a proper method of treatment for a patient suffering from a food-borne pathogen disease as well as for developing new methods of treatment.

In some other embodiments, the present invention concerns different methods for analyzing DNA isolated from a pathogenic microorganism. Such DNA analysis may include a test to determine which of the known pathogenic microorganisms has caused a particular disease in a patient. In other embodiments, such analysis may be used to isolate and clone new pathogenic microorganisms. The results of the analysis may be used to determine a proper method of treatment for a patient suffering from an infectious disease as well as for developing new methods of treatment.

Different methods of DNA analysis for the purposes of identification of a food-borne pathogen or any other pathogenic microorganism, including, without the limitation, DNA cloning, Southern blot analysis, slot-blot analysis, in situ hybridization, DNA sequencing, hybridization with a probe, incubation with a fluorescent dye, PCR, real-time PCR, DNA chromatography, flow-cytometry, in vitro transcription and/ or in vitro translation as well as various reactions with different DNA binding proteins including such proteins as antibodies.

In one embodiment, DNA isolated from a food-borne pathogen or other pathogenic microorganism can be analyzed by PCR. As little as 30 genomic DNA targets could be detected by PCR on a DNA template prepared according to the methods of the instant invention.

In another embodiment, DNA isolated according to the methods of the instant invention can be analyzed by a real-time polymerase chain reaction (real-time PCR), also called quantitative real time polymerase chain reaction (qPCR) or kinetic polymerase chain reaction. Real-time PCR is a laboratory technique based on the polymerase chain reaction used to amplify and simultaneously quantify a targeted DNA molecule. It enables both detection and quantification (as absolute number of copies or relative amount when normalized to DNA input or additional normalizing genes) of a specific sequence in a DNA sample.

Real-time PCR quantifies the amplified DNA as it accumulates in the reaction in real time after each amplification cycle. Two common methods of quantification are used: 1) fluorescent dyes that bind to double-stranded DNA, and 2) modified DNA oligonucleotide probes that fluoresce when hybridized with a complementary DNA. In setting up real-time PCR conditions, a person skilled in the relevant art may follow U.S. Pat. Nos. 5,210,015, 5,487,972 and 6,300,069; teachings of which incorporated in this disclosure by reference.

Figure 2:
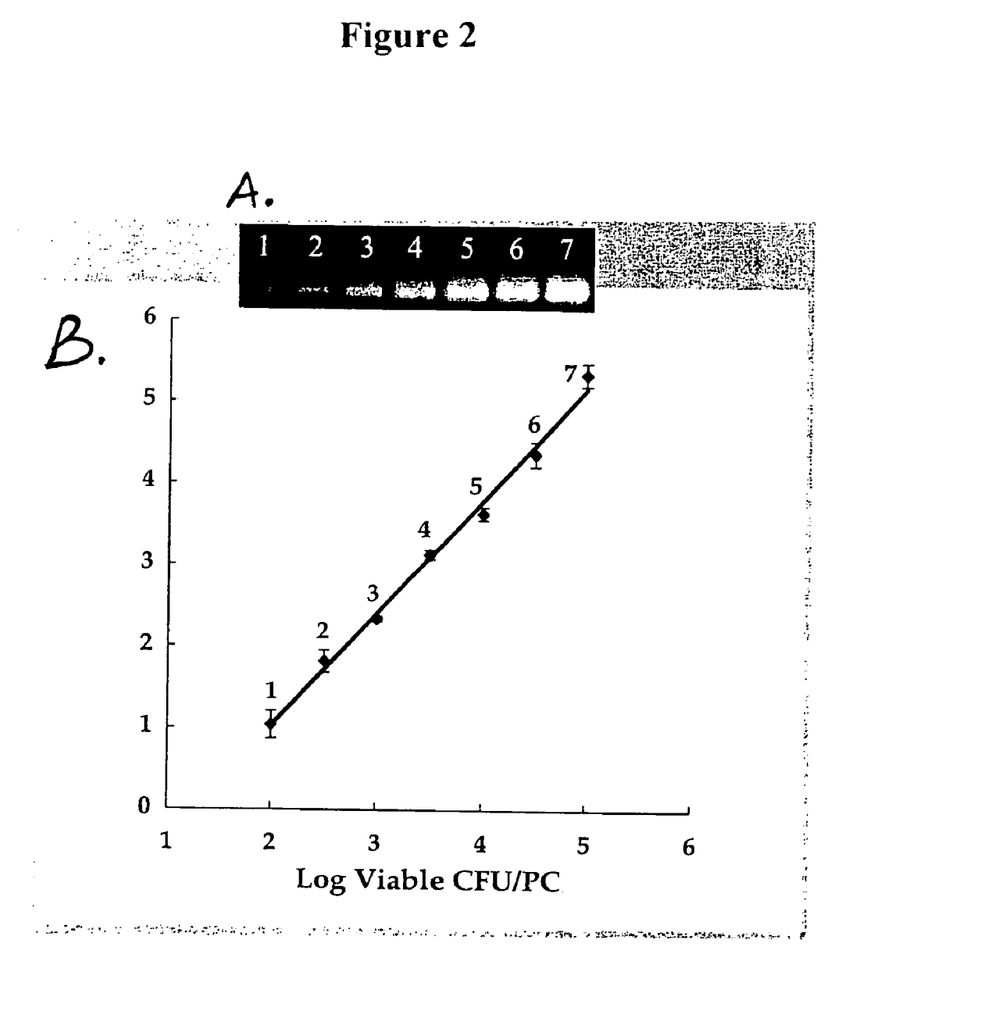
Figure 3:
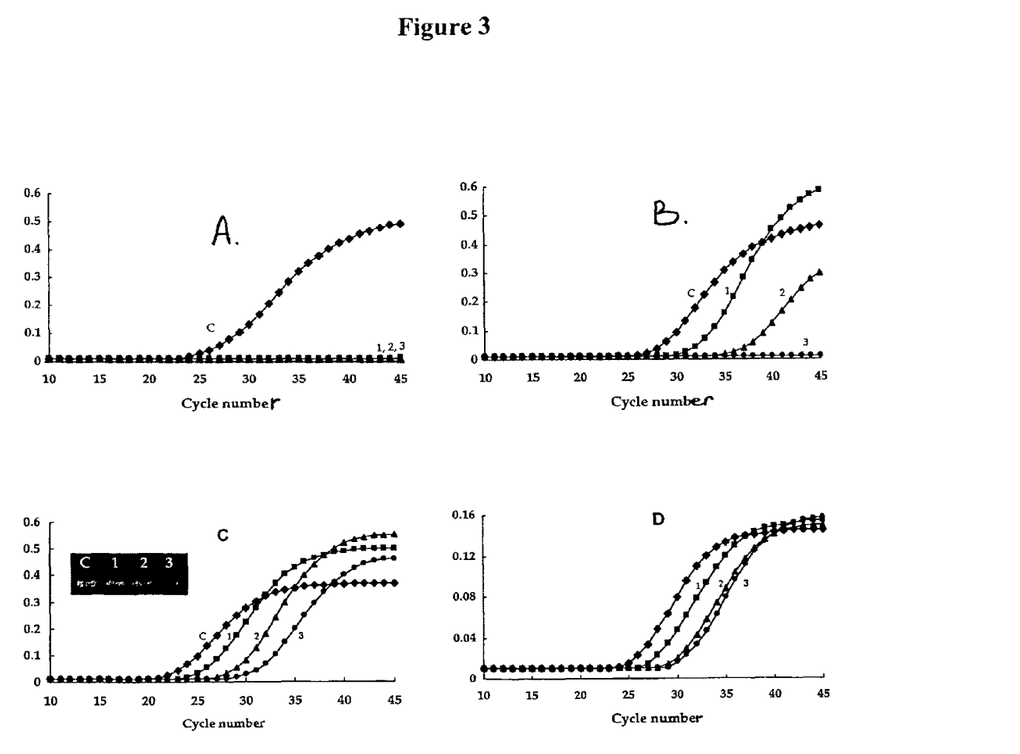

In one embodiment of the instant invention, real-time PCR can be used to analyze DNA isolated from food-borne pathogens or other pathogenic microorganisms. In at least some embodiments of the instant invention, real-time PCR can be used to selectively amplify DNA from live bacterial cells which are admixed with dead cells. In one example, ethidium bromide monoazide (EMA) methodology for PCR is utilized to distinguish between live and dead cells. As shown in FIG. 2, when live cells are admixed with heat-inactivated cells in different ratios, the intensity of the relative fluorescence of amplified DNA correlates with the proportion of live cells in a sample (compare lines 1 and 7 of FIG. 2A, also see FIG. 2B). As also shown in FIG. 3, if cells are γ-irradiated with the increased intensity of radiation, the amplification of DNA in the samples decreases proportionally to the increase in the number of radiation-damaged cells.

Because these real-time PCR methods can selectively detect and measure a proportion of live bacterial cells in a mixture of live and dead cells, these methods are highly valuable in monitoring progress in killing live food-borne pathogens in a great variety of samples. In some embodiments, the above-described real-time PCR procedure can be used to determine the minimal amount of an antibiotic required to efficiently destroy all live bacterial cells in a particular food sample or to identify which of the several different antibiotics is the most efficient in killing a particular food-borne pathogen in a particular food sample. In other embodiments, the above-described real-time PCR procedure can be used to determine a minimal time required for destroying food-borne pathogens in a sample by such means, as for example, UV irradiation or pasteurization.

Figure 4:
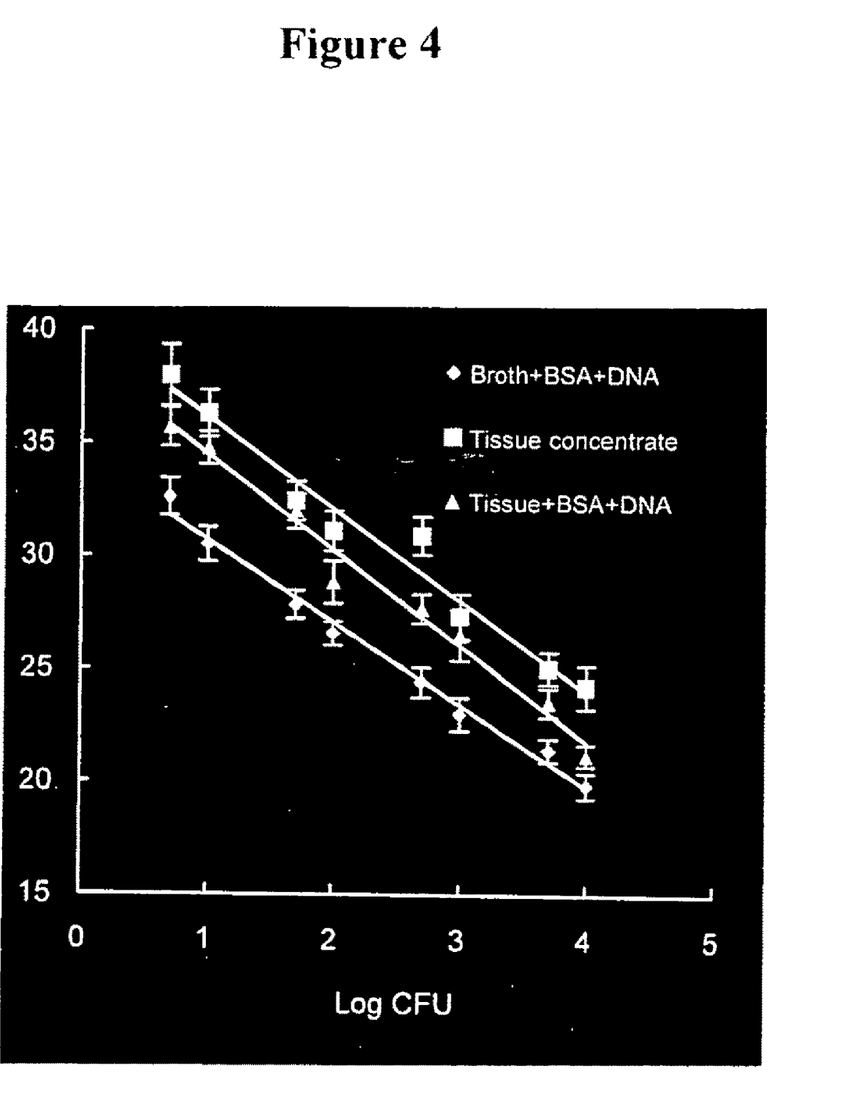

In some embodiments of the instant invention, the real-time PCR methods can be used for detecting low numbers of pathogenic microorganisms in a wide variety of foods, clinical specimens, and environmental samples that exhibit high levels of PCR inhibition because as few as 12.5 genomic targets, which correspond to 5 CFU per one gram of an initial sample, can be detected per one real-time PCR reaction when the methods of the instant invention are used (see FIG. 4 and further description below).

In at least some of its embodiments, the instant invention concerns improved methods for DNA isolation. These methods isolate sufficiently pure bacterial DNA when the starting number of bacterial cells is limited. According to at least some embodiments of the instant invention, a carrier DNA and bovine serum albumin (BSA) are added prior to bacterial DNA extraction from the sample. In at least some of the embodiments, a carrier DNA is Salmon Sperm DNA which can be used in final concentrations from 1 μg/ul to 100 μg/ul, while BSA can be used in a final concentration from 3 μg to 100 μg. Other compounds can be used in addition to or instead of Salmon Sperm DNA and BSA as DNA carriers. Such compounds include, but are not limited to, natural polymers, synthetic polymers, high molecular weight DNA, yeast genomic DNA, synthetic polypeptides, purified polypeptides and proteins.

In real-time PCR, a threshold level of emission above the baseline is selected and the point at which the amplification plot crosses the threshold is defined as the Ct value (Levin, 2004). The threshold is usually set at 10 times the standard deviation of the baseline. A plot of the log genomic units against the resulting Ct values yields a straight line. As can be seen in FIG. 4, the threshold for detecting DNA isolated from bacterial cells was decreased when DNA isolation was performed in the presence of BSA and Salmon Sperm DNA.

The methods and compositions of the present disclosure may be utilized to process samples larger than conventional samples. For example, sample sizes up to and including about 500 grams may be processed according to the present disclosure. In one example, samples are obtained from, for example, a field of produce, such as, but without limitation, lettuce. Samples of lettuce leaves from various parts of the field are obtained in an amount, for example, of about 25 grams. The samples from the various parts of the field are then combined to yield a sample size of about 250 grams to about 500 grams. The resultant combined sample is processed according to the methods of the present invention described herein.

The invention will be more fully understood by reference to the following examples. These examples should not, however, be construed as limiting the scope of the invention.

EXAMPLE 1

Preparation of Activated Charcoal

Washing charcoal is an important step in preparing activated charcoal coated with bentonite. Activated carbon 1 to 2 mm particles (Filtrasorb 200, cat. no. 7440-44-O, Calgon Carbon Corp., Pittsburgh, Pa., USA) were washed several times in bulk with deionized water ($dH_2O$) in a 400 ml beaker until the drained water became clear. Washed activated carbon (30 ml packed wet volume in a 100 ml graduated cylinder, 16.3 dry weight) was then mixed with bentonite prepared as described below.

EXAMPLE 2

Coating of Activated Charcoal with Bentonite

Four grams of bentonite were added to 200 ml of deionized water ($dH_2O$) in a blender jar. The mixture was then blended at high speed for 1 minute to break up large lumps. The resulting bentonite suspension was then poured into a 250 ml centrifuge bottle and was centrifuged at 700 rpm for 1 minute. Upon completion of the centrifugation, 130 ml of the top bentonite suspension was measured and poured into a large (2 L) beaker. 30 ml of wet washed activated charcoal were then added to the suspension and the beaker was coated with foil. The mixture in the beaker was then shaken at 150 rpm for 12 hours at 37° C. and then removed to 55° C. for 3-4 hours or until activated charcoal coated with bentonite dried completely.

EXAMPLE 3

Preparation of β-Cyclodextrin

10% solution of β-cyclodextrin was prepared by dissolving β-cyclodextrin powder in distilled water. Just prior to use, the solution was warmed over a Bunsen burner to thoroughly dissolve β-cyclodextrin. The resulting solution can then be stored temporarily (1-2 hours) at 55° C. to prevent precipitation.

EXAMPLE 4

Preparation of Shellfish Tissue Samples

Canadian oysters (*Crassostrea gigas*) were purchased from local retail sources. Shellfish tissue (10 g) was blended with 90 ml of sterile 0.85% saline in a blender. The resulting homogenates were frozen at −20° C. and thawed three times to ensure that no viable cells of *E. coli* were present. The homogenized and repeatedly thawed samples were then cultured for *E. coli* by smear plating of 0.1 ml onto duplicate plates of Levine's Eosine Methylene Blue Agar (EMB, Difco), followed by incubation at 37° C. for 24 hours. The fresh homogenates were also examined for the presence of *E. coli* O157:H7 by non-selective enrichment.

EXAMPLE 5

Bacterial Strain and Growth Conditions

*E. coli* O157:H7 strain 9490 was obtained from The Centers for Disease Control, Atlanta Ga. 30333, USA and was used throughout these studies. All media were from Difco. In order to obtain exponential growth phase cultures, *E. coli* O157:H7 was inoculated from a Tryptic Soy Agar (TSA) slant into a tube containing 10 ml of Tryptic Soy broth plus 0.5% glucose (TSB$^+$) and incubated with rotary agitation (250 rpm) at 37° C. overnight. A portion of this culture (5 ml) was then transferred to 100 ml of TSB$^+$ in a 250 ml flask and incubated at 37° C. with rotary agitation (250 rpm) for 4 h to obtain mid-log phase cells ($A_{600}$ nm-1.7 in 1 cm path length cuvettes). Cells were then harvested by centrifuging 16,000×g for 10 min at 4° C. The pellet was washed with 30 ml of 0.85% saline, pelleted again and resuspended in 30 ml of saline. Final cell densities (~1.2×10$^9$ CFU/ml) were determined by smearing 0.1 ml of decimal dilutions in saline onto the surface of duplicate TSA plates. Plate counts were then correlated with $A_{600}$ nm readings of cell suspensions.

EXAMPLE 6

The Recovery of *E. coli* O157:H7 from Charcoal Coated with Bentonite at Different pH Values Cells of *E. coli* O157:H7 (3×10$^4$ CPU) were suspended in 22 ml of 0.01 M acetate buffered saline (0.85% NaCl, acetic acid:sodium acetate, pH 4.0, 5.0, and 6.0) or in 22 ml of 0.01 M phosphate buffered saline (0.85% NaCl, Na$_2$HPO$_4$.7H$_2$0: NaH$_2$PO$_4$, pH 7.0 and 8.0). The cell suspension was treated with activated charcoal as described below.

Approximately 3.0×10$^4$ CFU of *E. coli* O157:H7 were suspended in 22 ml 0.01 M acetate buffered saline (0.85% NaCl, acetic acid:sodium acetate, pH 5.0; ABS). The optimized amount of bentonite (1.52 g) was used to coat 16.3 g of activated carbon.

Dry activated carbon coated with bentonite (4.6 g) was transferred to a sterile 250 ml beaker and washed twice with 20 ml of sterile saline. The 22 ml cell suspension was mixed with the washed activated carbon and the preparation was incubated at room temperature with rotary agitation (160 rpm) for 15 min. Sterilized glass wool (0.2 g) was placed at the bottom of a 50 ml inverted sterile syringe barrel. The preparation consisting of activated carbon coated with bentonite and suspended cells was transferred to the inverted syringe barrel and then eluted with ABS saline until 22 ml was collected in a sterile graduated cylinder. Portions (0.1 ml) were then smear plated onto the surface of duplicate EMB plates which were then incubated at 37° C. for 24 hours. Control samples were treated similarly but with activated carbon not coated with bentonite.

The amount of bentonite used to coat the activated carbon significantly affected the recovery of *E. coli* O157:H7 (FIG. 1 and also Table 3). When 4.2 g of activated carbon was coated with 0.4 g of bentonite and the pH value of the cell suspension was adjusted to 5.0, the recovery of *E. coli* O157:H7 was 91.6±4.4% (FIG. 1).

As shown below in Table 3, about 90% of in-put food-borne microorganisms may be recovered after incubation with activated charcoal coated with bentonite, while virtually no food-borne microorganisms are recovered after incubation with uncoated charcoal.

TABLE 3

Recovery of *E. Coli* O157:H7 cells from Charcoal Coated with Bentonite in Comparison to Uncoated Charcoal

| No. of In-put CFU Per 0.1 ml (control) | Percent CFU Recovered From Uncoated Charcoal | Percent CFU Recovered From Coated Charcoal |
| --- | --- | --- |
| 133 | 0 | 92.5 ± 4.4 |
| 128 | 0 | 94.2 ± 3.7 |
| 149 | 0 | 88.1 ± 6.8 |
| 142 | 0 | 91.6 ± 3.5 |
|  |  | Mean 91.6 ± 4.6 |

As can be further seen from FIG. 1, the ratio of bentonite to activated charcoal determines the efficiency of recovery for food-borne microorganisms with almost no microorganisms being recovered from uncoated charcoal and only about 30% of microorganisms being recovered when the ratio of bentonite to activated charcoal is 1:66. However, as also can be seen from FIG. 1, the percentage of recovered microorganisms increases to 90% once the ratio of bentonite to activated charcoal is 1:16 or lower.

The recovery of *E. coli* O157:H7 was also affected by pH. As can be seen from Table 2, when cell suspensions of *E. coli* O157:H7 were adjusted to pH 4.0, 5.0, 6.0, 7.0 and 8.0 respectively before treatment with activated charcoal coated with bentonite, the highest recovery of *E. coli* O157:H7 was 91.6±4.4% at pH 5.0.

EXAMPLE 7

Removal of PCR Inhibitors from Seeded Oyster Tissue with Activated Charcoal Coated With Bentonite

*E. coli* O157:H7 was serially diluted in 0.85% saline to yield 5.0×10$^2$, 1.5×10$^3$, 5.0×10$^3$, 1.5×10$^4$, 5.0×10$^4$, 1.5×10$^5$, 5.0×10, 1.5×10$^6$, 5.0×10$^6$, and 1.5×10$^7$ CFU/ml. A portion (1 ml) of each of the above cell suspensions was seeded in duplicate into 100 ml (10 g) of oyster tissue homogenate in 250 ml centrifuge bottles which were then vigorously agitated. Each preparation was then centrifuged at 1000 rpm (164×g) for 5 min to pellet large particles of tissue. The supernatant from each preparation was then centrifuged at 10,000 rpm (16,000×g) for 10 min to obtain a pellet containing the target cells. The pellet was then resuspended in 22 ml 0.01 M ABS and treated with activated charcoal coated with bentonite as described above, and transferred to an inverted 50 ml syringe barrel. The 22 ml cell suspension was eluted with ABS from the syringe barrel and was then centrifuged at 10,000 rpm (16,000×g) for 10 min to pellet the target cells. The final pellet was resuspended with 0.5 ml of $dH_2O$ in a 2 ml microcentrifuge tube and mixed with 0.5 ml of double strength TZ lysing solution (4% Triton X-100, 5 mg/ml sodium azide, 0.2M Tris-HCl, pH 8.0). The tubes were then heated in a boiling water bath for 10 min to lyse the cells. The cell lysates were then cooled to room temperature and centrifuged at 13,400 rpm (12,100×g) for 5 min. A portion of each supernatant DNA sample (19.8 μl) was then added to a conventional PCR mixture so as to total 25 μl which was subjected to thermal cycling as described below.

EXAMPLE 8

DNA Purification with the Aid of Commercial Kits and Resins

The Wizard® DNA Clean-Up System (Promega, cat. no A7170) was used to remove PCR inhibitors in oyster samples and to yield 40 μl of purified DNA. The procedure was performed according to the manufacturer's instructions. The DNA samples were used immediately or stored at −20° C.

With the Chelex-100 resin, homogenized tissue samples were subjected to differential centrifugation as follows: 0.5 ml of 10% Chelex-100 resin (cat no. 142-2832, Bio-Rad) suspended in $dH_2O$ was added to 0.5 ml of cell pellets suspended in 2×TZ lysing solution in a 2 ml microcentrifuge tube. The procedure described by Rodriguez-Lazaro et al. (2004) yielding 1.0 ml of purified DNA was then followed. After differential centrifugation the QIAamp® DNA Mini Kit (cat. no. 51304 QIagen®) was utilized for DNA purification according to the manufacture's instructions yielding 200 μl of purified DNA.

EXAMPLE 9

Conventional PCR Detection of the rjbE Gene

A 149 bp fragment of the rfbE gene of *E. coli* O157:117 was used for PCR detection. The primer sequences were O157 hf 5'-AAA TAT AAA GGT AAA TAT GTG GGA ACA TTT GG-3' (SEQ ID NO: 1) and O157 br 5'-TGG CCT TTA AAA TGT AAA CAA CGG TCA T-3' (SEQ ID NO: 2) (Fortin et al., 2001). Primers were synthesized by Sigma Genosys (The Woodlands, Tex., USA). Following optimization, the PCR mixture (total volume of 25 ul) consisted of 1 unit of DNA polymerase (cat no. BIO-21042, Bioline USA Inc., Randolph, Mass., USA), 1×PCR reaction buffer (cat no. BIO-21042), 200 μM $MgCl_2$, 200 μM (each) dATP, dCTP, dGTP and dTTP, each PCR primer at a concentration of 0.1 μM, and template DNA 19.8 μl. Thermocycling was performed in a Techgene thermocycler (FTGENE 5D, 112757-4, Techne Cambridge LTD. DUXFORD, Cambridge UK) with the following PCR cycling conditions: initial denaturation at 96° C. for 5 min, followed by 40 cycles, each consisting of 30 s at 9° C., 30 s at 59° C. and 30 s at 72° C. and final extension for 7 min at 72° C. PCR product was separated by electrophoresis in 1.5% agarose gel at 130 V for 20 min in boric acid buffer (5 mM disodium borate decahydrate, pH adjusted to 8.5 with 5 mM boric acid) according to Brody and Kern (2004). The amplified PCR product was detected with Gelstar® Nucleic Acid Gel Stain (cat. no 50535, Cambrex Bio Science Rockland, Main, USA). An unspiked oyster sample was always included as a negative control.

EXAMPLE 10

Effect of Oyster Inhibitors on Detection of Bacteria by PCR

To assess the effect of oyster inhibitors on the detection of *E. coli* O157:H7 by the PCR, broth cultures were serially diluted with 0.85% saline and spiked into 100 ml of oyster homogenates to yield various CFU (colony forming unit) levels. PCR templates were prepared by the same method as described above. The detection limit in pure culture was $5.0×10^2$ CFU/ml which was equivalent to 10 genomic targets per PCR reaction, whereas the detection limit with oyster samples which were not treated with activated charcoal coated with bentonite was $1.5×10^5$ CFU/g of oyster tissue, equivalent to $3.0×10^4$ genomic targets per PCR reaction. There was a $3.0×10^3$ fold difference between the limit of sensitivity with cells from a pure culture and cells from untreated oyster tissue.

When samples obtained from seeded oyster homogenates without enrichment were purified with the aid of the Wizard® DNA Clean-Up System and the Chelex® 100 Resin, the minimum level of detection was $1.5×10^3$ genomic targets/g of oyster tissue, which is equivalent to 300 genomic targets per PCR reaction. The use of the QIAamp® DNA Mini Kit resulted in a minimum detection limit of $5.0×10^2$ genomic targets/g of oyster tissue, which is equivalent to $5×10^2$ genomic targets per PCR reaction.

The treatment of samples without enrichment, derived from seeded oyster homogenates, with activated carbon coated with bentonite yielded a minimum PCR detection level of $1.5×10^2$ genomic targets per gram of oyster tissue which was equivalent to 30 CFU per PCR reaction.

EXAMPLE 11

Extraction of Food-Borne Pathogens from Ground Meat 25 grams of ground beef and 75 ml of saline (0.85% NaCl) were blended together for 30 seconds at normal setting in a small stomacher bag with filter membrane. 100 ml of 10% β-cyclodextrin in $dH_2O$ was then added to the mixture and it was blended for 2 minutes at high setting. The resulting suspension was poured into a 250 ml sterile centrifuge bottle and centrifuged for 5 minutes at 1,000 rpm at room temperature (20-30° C.). The resulting supernatant was then carefully removed with a pipette to a new centrifuge bottle and centrifuged for 10 minutes at 10,000 rpm at 4° C. Using a pipette, a supernatant was gently removed and discarded, while the pellet was saved and recovered by resuspending in 27 ml of sterile saline and adding sterile 0.85% saline buffered with acetic acid to a resulting pH of 5.0 (0.01M acetic acid/L $dH_2O$ stock was used to adjust saline). The suspended pellet was then collected with a pipette and placed together with 4.6 g of the above prepared charcoal coated with bentonite (see Example 2) into a 250 ml beaker. The mixture was then washed with 20 ml of sterile saline 2 or 3 times. The 30 ml of the collected pellet was then added to the beaker and mixed at 150-160 rpm on a shaker for 15 minutes at room temperature.

0.2 g of glass wool was then placed at the bottom of a 60 ml plastic syringe and the charcoal was gently transferred into the syringe with a long spatula. The liquid from the beaker was then slowly poured down the spatula onto the charcoal and passed through the syringe. The output liquid was then collected in a sterile graduated cylinder and if necessary, more acetate buffered saline was added in order to bring the volume of the output liquid to a total of 30 ml. The liquid was then transferred to a 50 ml centrifuge tube and centrifuged 10 minutes at 10,000 rpm at 4° C. After centrifugation was completed, supernatant was removed and discarded, while the pellet was resuspended in 1 ml of saline and transferred to a microcentrifuge tube which was then centrifuged for 5 minutes at 12,000 rpm. After centrifugation was completed, the resulting supernatant was discarded and the pellet was saved.

EXAMPLE 12

DNA Isolation From Small Amounts of Bacteria

After food-borne pathogen was collected from a food sample (see e.g. Example 10), it was resuspended in 500 µl of dH$_2$O containing 0.3 mg BSA and 0.01 mg of salmon sperm DNA; 500 µl of 2×TZ lysing solution (4% Triton X-100, 5 mg/ml sodium azide, 0.2M Tris-HCl, pH 8.0) was then added to the suspension. The mixture was then boiled for 10 minutes to disrupt the cells and release the DNA and it was then cooled down to room temperature and centrifuged for 5 minutes at 13,400 rpm to remove debris from lysed cells. 1000 microlitters of the resulting liquid was then carefully pipetted to a new sterile microcentrifuge tube and 1000 µl of chilled absolute ethanol was then added to precipitate DNA. The mixture was then centrifuged for 15 minutes at 12,000 rpm and the resulting supernatant was discarded. The pellet was then resuspended in 100 µl of dH$_2$O and centrifuged for 5 minutes at 12,000 rpm. 10 µl of the top supernatant then can be used for a real-time PCR reaction in which as little as 5 CFU/g or 12.5 genomic targets per PCR can be detected.

charide O side chain of *E. coli* O157 strains and were O157 BF 5'-AAA-TAT-AAA-GGT-AAA-TAT-GTG-GGA-ACA-TTT-GG-3' (SEQ ID NO: 1) and O157 BR 5'-TGG-CCT-TTA-AAA-TGT-AAA-CAA-CGG-TCA-T-3' (SEQ ID NO: 2) (Fortin et al., 2001). The primers were synthesized by Sigma Genosys (The Woodlands, Tex., USA). The real-time thermocycler used in this study was a DNA Engine Opticon® system (MJ Research Corp., Waltham, Mass., USA). The RT-PCR reaction mixture consisted of 12.5 µl of 2× iQ™ SYBR® Green mixture (cat. no. 170-8882, Bio-Rad, Hercules, Calif., USA), 0.6 µl of 10 µM of each primer, 5 µl sample, and 6.3 µl of deionized water. The 2× iQ™ SYBR® Green mixture consisted of 400 µM of each dNTP, 50 U/ml of Taq polymerase, 6 mM MgCl$_2$, 100 mM KCl, and 40 mM Tris-HCl at pH 8.4. RT-PCR was performed with initial denaturation at 95° C. for 5 min, followed by 40 cycles of denaturation at 94° C. for 25 s, primer annealing at 52° C. for 25 s, and primer extension at 72° C. for 30 s. All of the real-time PCR assays were conducted three times with the mean values and standard deviations reported.

While the foregoing has described what are considered to be the best mode and/or other examples, it is understood that various modifications may be made therein and that the subject matter disclosed herein may be implemented in various embodiments, forms and examples, and that the teachings may be applied in numerous applications, only some of which have been described herein. The present examples and embodiments, therefore, are to be considered in all respects as illustrative and not restrictive, and the invention is not to be limited to the details given herein. It is intended by the following claims to claim any and all applications, modifications and variations that fall within the true scope of the present teachings.

SEQUENCE LISTING

```
<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaatataaag gtaaatatgt gggaacattt gg                                    32

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tggcctttaa aatgtaaaca acggtcat                                        28
```

EXAMPLE 13

Real-Time PCR

The PCR primers used to amplify a 149 bp fragment of the rfbE gene that codes for the production of the lipopolysac-

What is claimed is:

1. A method for removing polymerase chain reaction (PCR) inhibitors from a sample comprising a pathogenic microorganism, comprising incubating the sample with activated charcoal coated with bentonite; and removing PCR inhibitors from the sample prior to DNA extraction from the microorganism and performance of DNA analysis.

2. The method of claim 1, wherein said sample is selected from the group consisting of a food sample, human tissue, human fluids, animal tissue, animal fluids, plant tissue, clinical specimen and environmental specimen.

3. The method of claim 1, wherein said DNA analysis includes at least one of the following: DNA cloning, Southern blot analysis, slot-blot analysis, in situ hybridization, DNA sequencing, hybridization with a probe, incubation with a fluorescent dye, PCR, real-time PCR, DNA chromatography, flow-cytometry, in vitro transcription, in vitro translation, binding reactions with antibodies or binding reactions with proteins.

4. The method of claim 1, wherein the sample is incubated with activated charcoal coated with bentonite at a pH in the range from about 5 to about 8.

5. The method of claim 1, wherein the sample is incubated with activated charcoal coated with bentonite by passing the sample at least once through a column packed with activated charcoal coated with bentonite.

6. The method of claim 1, wherein the weight ratio of said sample to said charcoal is in the range from about 1:1 to about 20:1.

7. The method of claim 1, wherein the sample is incubated with β-cyclodextrin prior to incubation with activated charcoal coated with bentonite.

8. The method of claim 7, wherein the incubation of said sample with β-cyclodextrin is performed by completing the following steps:
homogenizing said sample with said β-cyclodextrin for about 1 to about 10 minutes at room temperature;
centrifuging the resulting homogenate at about 1,000 rpm to about 3,000 rpm during about 1 to about 5 minutes; and
collecting a supernatant comprising the pathogenic microorganism.

9. The method of claim 1, wherein the sample is incubated with a solution of cyclodextrin prior to incubation with activated charcoal coated with bentonite and said cyclodextrin is selected from the group consisting of α-cyclodextrin, β-cyclodextrin and γ-cyclodextrin.

10. A method for isolating a microorganism from a food sample, animal tissue, human tissue, human fluids, plant tissue, environmental or clinical specimen, said method comprising the following steps:
homogenizing one weight part of sample, tissue, fluids or specimen in 2 to 10 parts of saline comprising from 0.2% to 1.0% of sodium chloride;
adding a β-cyclodextrin solution to the homogenized sample;
blending the mixture of homogenized sample and β-cyclodextrin solution to homogeneity;
centrifuging the homogenized mixture at about 1,000 rpm to about 3,000 rpm for about 1 to about 5 minutes;
collecting a supernatant fraction after centrifugation of the homogenized mixture;
centrifuging the supernatant fraction at about 8,000 rpm to about 15,000 rpm for about 5 to about 10 minutes at about 4° C. and obtaining a liquid fraction and a pellet;
discarding the liquid and resuspending the pellet in sterile saline and obtaining a suspension;
adjusting the pH of the resulting suspension to a pH in the range from about 4.5 to about 6;
incubating the suspension with activated charcoal coated with bentonite;
centrifuging the suspension after incubation at about 8,000 rpm to about 15,000 rpm for about 5 to about 20 minutes and obtaining a second pellet; and
resuspending the second pellet in a sterile saline;
wherein the resuspended second pellet comprises the isolated microorganism.

11. A method of claim 10 further comprising:
extracting DNA from the isolated microorganism, comprising the following steps:
releasing DNA from the microorganism by boiling the isolated microorganism in a solution comprising 2% Triton X-100, 2.5 mg/ml sodium azide, 0.1 M Tris-HCl, pH 8.0; and
precipitating the resulting DNA with chilled ethanol.

12. The method of claim 11, wherein the solution further comprises a DNA carrier selected from the group consisting of BSA, high molecular weight DNA, yeast genomic DNA, salmon sperm DNA and a combination of any of these carriers.

13. A method for identification of a live microorganism in a food sample, animal tissue, human tissue, human fluids, plant tissue, environmental or clinical specimen, said method comprising the following steps:
homogenizing a food sample, tissue, environmental or clinical specimen comprising a pathogenic microorganism with saline;
incubating the resulting homogenate with β-cyclodextrin;
centrifuging the mixture of homogenate and β-cyclodextrin at about 1,000 to about 3,000 rpm for about 3 to about 15 minutes and obtaining a supernatant and a pellet;
collecting the supernatant;
centrifuging the supernatant at about 8,000 to about 15,000 rpm for about 5 to about 20 minutes to obtain a second pellet;
resuspending the second pellet obtained from centrifugation of the supernatant in sterile saline thereby obtaining a suspension;
incubating the suspension with activated charcoal coated with bentonite and collecting the resulting supernatant;
centrifuging the resulting supernatant at about 8,000 to about 15,000 rpm for about 5 to about 20 minutes, thereby obtaining a third pellet;
washing the resulting third pellet and resuspending the third pellet in a lysing solution comprising 2% Triton X-100, 2.5 mg/ml sodium azide, 0.1 M Tris-HCl, pH 8.0;
boiling the mixture of the third pellet and lysing solution;
centrifuging the mixture of the third pellet and lysing solution, thereby obtaining a second supernatant and a fourth pellet;
precipitating DNA of the pathogenic microorganism from the second supernatant with chilled ethanol;
washing the precipitate;
resuspending the precipitate in water, wherein the precipitate comprises DNA of the pathogenic microorganism; and
performing real-time PCR on the DNA, wherein the intensity of real-time PCR correlates with the presence of a live microorganism in the sample, tissue, fluid, or specimen.

14. A method for identification of an optimal dosage of an antibiotic or other agent required to eliminate a live microorganism, in which the following steps are performed:
performing treatments with various dosages of the antibiotic or other agent and recording the dosage used in each treatment;

obtaining a set of food samples, tissues, environmental or clinical specimens, said set comprising food samples, environmental or clinical specimens which were collected after treatment with various dosages of the antibiotic or other agent;

performing the method of claim 13 on each of the samples or specimens in the set, thereby obtaining information about presence of a live microorganism and its quantity in each sample or specimen of the set;

interpreting the information obtained, thereby identifying a sample or specimen in the set in which no live microorganisms were present or only a minimal number of live microorganisms was present in comparison to other samples or specimens in the set; and identifying the dosage of the antibiotic or other agent recorded which corresponds to the sample or specimen identified, wherein the dosage identified is the optimal dosage required to eliminate the live microorganism.

15. A method for identification of an antibiotic or other agent suitable to eliminate a live microorganism, in which the following steps are performed:

performing treatments with various antibiotics or other agents and recording an antibiotic or other agent used in each treatment;

obtaining a set of food samples, environmental or clinical specimens, said set comprising food samples, environmental or clinical specimens which were collected after treatment with various antibiotics or other agents;

performing the method of claim 13 on each of the samples or specimens in the set obtained, thereby obtaining information about presence of a live microorganism and its quantity in each sample or specimen of the set;

interpreting the information obtained, thereby identifying a sample or specimen in the set in which no live microorganisms were present or only a minimal number of live microorganisms was present in comparison to other samples or specimens in the set; and identifying the antibiotic or other agent recorded which corresponds to the sample or specimen identified, wherein the antibiotic or other agent identified is suitable to eliminate the live microorganism.

16. A method for identifying a pathogenic microorganism in a sample, said method comprising the following steps:

incubating the sample with activated charcoal coated with bentonite;

extracting DNA from the microorganism of the incubated sample;

performing DNA analysis on the extracted DNA; and identifying the microorganism based on the results of the DNA analysis.

17. The method of claim 16, wherein said sample is selected from the group consisting of a food sample, human tissue, human fluids, animal tissue, animal fluids, plant tissue, clinical specimen and environmental specimen.

18. The method of claim 16, wherein said DNA analysis includes at least on of the following: DNA cloning, Southern blot analysis, slot-blot analysis, in situ hybridization, DNA sequencing, hybridization with a probe, incubation with a fluorescent dye, PCR, real-time PCR, DNA chromatography, flow-cytometry, in vitro transcription, in vitro translation, binding reactions with antibodies or binding reactions with proteins.

* * * * *